US008033985B2

(12) United States Patent
Smith

(10) Patent No.: US 8,033,985 B2
(45) Date of Patent: Oct. 11, 2011

(54) SEXUAL STIMULATION APPARATUS

(76) Inventor: Shannon Smith, Wollstonecraft (AU)

(*) Notice: Subject to any disclaimer, the term of this patent is extended or adjusted under 35 U.S.C. 154(b) by 157 days.

(21) Appl. No.: 12/310,898

(22) PCT Filed: Sep. 12, 2007

(86) PCT No.: PCT/AU2007/001357
§ 371 (c)(1), (2), (4) Date: Mar. 10, 2009

(87) PCT Pub. No.: WO2008/031160
PCT Pub. Date: Mar. 20, 2008

(65) Prior Publication Data

US 2009/0312599 A1 Dec. 17, 2009

(30) Foreign Application Priority Data

Sep. 12, 2006 (AU) ................................ 2006905029

(51) Int. Cl.
*A61F 5/00* (2006.01)

(52) U.S. Cl. ........................................................ 600/38

(58) Field of Classification Search .............. 600/38–41; 601/72, 80
See application file for complete search history.

(56) References Cited

U.S. PATENT DOCUMENTS

| | | | | |
|---|---|---|---|---|
| 5,853,362 | A | 12/1998 | Jacobs | |
| 6,533,718 | B1 | 3/2003 | Ritchie et al. | |
| 6,749,557 | B2 * | 6/2004 | Garland | 600/38 |
| 2002/0188233 | A1 * | 12/2002 | Denyes | 601/46 |
| 2005/0192519 | A1 * | 9/2005 | Crunick | 601/72 |

FOREIGN PATENT DOCUMENTS

| | | | |
|---|---|---|---|
| DE | 102005014123 | A1 | 9/2006 |
| JP | 2003-088563 | A | 3/2003 |
| JP | 2005-288079 | A | 10/2005 |

* cited by examiner

*Primary Examiner* — Samuel Gilbert
(74) *Attorney, Agent, or Firm* — Abelman, Frayne & Schwab

(57) ABSTRACT

A sexual stimulation apparatus comprising a phallic shaped member having a handle disposed at its base. The handle has a convex surface substantially facing away from the phallic shaped member. The convex surface has at least one projection member extending therefrom. In use, the convex surface sits snugly against the palm and fingers of a user's hand, and the projection member interdigitally engages with the user's hand.

18 Claims, 4 Drawing Sheets

SEXUAL STIMULATION APPARATUS

RELATED APPLICATIONS

The present application claims priority of PCT/AU 2007/001357 having International Filing date 12 Sep. 2007 and Australian Application No. AU 2006 905029 having filing date 12 Sep. 2006.

TECHNICAL FIELD

The present invention relates to a sexual stimulation apparatus and particularly to a sexual stimulation apparatus designed for use by women to increase their personal comfort when using the sexual stimulation apparatus during masturbation.

BACKGROUND ART

Sexual stimulation apparatus are well known and have been commercially available for many decades. Conventional sexual stimulation apparatus include dildos, vibrators and the like and are typically made from plastic, metal, silicone, rubber or other similar materials. Conventional sexual stimulation apparatus have a straight or curved shaft that is typically shaped to resemble a phallus. The shaft typically does not include a handle and at best, the shaft may include a bulbous end to assist in a user gripping the sexual stimulation apparatus during use.

However, because the shaft of a conventional sexual stimulation apparatus does not include a handle, it is difficult for a user to grip a conventional sexual stimulation apparatus comfortably during use. This can be particularly problematic for women when using conventional sexual stimulation apparatus because of the anatomical position of a woman's vagina in relation to their arms and hands. Thus, a user, and particularly a female user, may experience tension, fatigue, discomfort or pain in their wrist, upper arm, shoulder and/or back when using a conventional sexual stimulation apparatus when masturbating.

Without a handle, a conventional sexual stimulation apparatus is difficult to hold comfortably by a user, and particularly a female user, with their wrist in a natural and comfortable orientation. It is difficult for a female user of a conventional sexual stimulation apparatus to insert the conventional sexual stimulation apparatus comfortably into their own vagina during masturbation and keep their wrist in a natural and comfortable orientation.

US 2002/0188233 (Denyes) describes a vibrating stimulation device, which an individual user cannot easily or comfortably use when masturbating. The shape and configuration of the Denyes vibrating stimulation device requires that a second operator uses the device on their partner. The "gun-shaped" handle of the Denyes device does not provide an individual user with any ergonomic benefits and does not allow an individual user to utilise the "palms down" technique when in use, which allows a single user to access her vagina whilst she is in a comfortable and ergonomically beneficial orientation.

U.S. Pat. No. 5,853,362 (Jacobs) describes an intravaginal glandular stimulation device, which an individual user cannot easily use during masturbation with a "palms down" technique. Whilst the intravaginal glandular stimulation device of Jacobs does include a handle the handle is used merely to "grasp" the device and the handle does not ergonomically contour with the individual user's hand nor does the handle sit snugly against the palm and finger's of the user's hand.

The intravaginal glandular stimulation device of Jacobs is specifically designed for G-Spot induced orgasm and thus clitoral stimulation is not a priority of the Jacobs device. Many women have reported that they find it easier to achieve orgasm when both the vagina and the clitoris are stimulated. The Jacobs device also does not have a definitive end portion and is therefore not intended to be fully inserted into an individual user's vagina or anus. In this way, the Jacobs device is most effective when used by two people simultaneously. The Jacobs device is adapted to simultaneously stimulate two users at once and accordingly has two insertable ends.

Therefore, it is an object of the present invention to provide an improved sexual stimulation apparatus which goes at least some way towards overcoming or minimising the prior art problems or limitations outlined above or at least providing an alternative thereto.

DISCLOSURE OF INVENTION

According to a first aspect of the present invention there is provided a sexual stimulation apparatus comprising a phallic shaped member having a handle disposed at its base, characterised in that said handle has a convex surface substantially facing away from said phallic shaped member and said convex surface has at least one projection member extending therefrom, wherein in use said convex surface sits snugly against the palm and fingers of a user's hand, and said projection member interdigitally engages with said user's hand.

Preferably, said handle and said phallic shaped member are integrally formed from a single piece of material.

Preferably, said single piece of material is injection moulded silicone.

Preferably, the sexual stimulation apparatus is adapted to be used with a "palms down" technique by an individual user, when used during masturbation.

Preferably, said handle and said phallic shaped member are formed from two separate pieces of material that are engageable with each other.

Preferably, said handle and said phallic shaped member are manufactured from the same material.

Preferably, said handle and said phallic shaped member are manufactured from different materials.

Preferably, said handle is manufactured from a rigid material and said phallic shaped member is manufactured from injection moulded silicone.

Preferably, said phallic shaped member is adapted to have batteries inserted in a cavity therein and said handle includes a vibrating mechanism whereby in use, said sexual stimulation apparatus vibrates to increase the sexual stimulation of said user.

Preferably, said handle is adapted to engage with a range of different phallic shaped members, each one of said range of different phallic shaped members having the same engagement means to allow it to engage with said handle.

Preferably, said projection member is substantially T-shaped when viewed in end view cross-section to facilitate engagement with said user's hand.

Preferably, said projection member is curved when viewed in side plan view to facilitate interdigital engagement with the fingers of said user's hand.

Preferably, said projection member includes a groove or channel therein to facilitate engagement with said user's fingers. Even more preferably, said groove or channel is curved and follows the natural contours of the user's fingers.

According to a second aspect of the present invention there is provided a hand-held sexual stimulation apparatus comprising in combination a phallic shaped member and clitoral stimulator, wherein the underside of said clitoral stimulator comprises a convex surface and at least one projection therefrom, wherein in use said convex surface sits snugly against the palm fingers of a user's hand, and said projection member interdigitally engages with said user's hand.

Preferably, said clitoral stimulator includes a plurality of spaced apart nodules.

Preferably, said plurality of spaced apart notches are different sizes and/or shapes.

Preferably, said clitoral stimulator further includes at least one cluster of nodules at or near an edge portion thereof, said cluster adapted to contact the clitoris of said user to promote sexual stimulation of the user.

Preferably, the sexual stimulation apparatus further includes an anal protruding member.

Preferably, the sexual stimulation apparatus further includes a testicle-shaped projection.

According to a third aspect of the present invention there is provided a hand-held personal sexual stimulation dildo having a handle disposed at its base, characterised in that said handle has a convex surface and at least one projection member extending therefrom, wherein in use said convex surface sits snugly against the palm and fingers of a user's hand, and said projection member interdigitally engages with said user's hand.

According to a fourth aspect of the present invention there is provided a handle adapted to be engaged with a phallic shaped member, said handle having a convex surface, said convex surface substantially facing away from said phallic shaped member when engaged therewith, said convex surface having at least one projection member extending therefrom, wherein in use said convex surface sits snugly against the palm and fingers of a user's hand, and said projection member interdigitally engages with said user's hand.

One preferred embodiment is defined as:

A sexual stimulation apparatus comprising in its upright orientation:

a. a handle having i. a body part with top and bottom surfaces and opposite ends and length along a central longitudinal axis, and width transverse said length, ii. a blade extending longitudinally and upward from said top surface of said body part, and having width less than width of said body part, iii. a roof part atop said blade and extending lengthwise and having width greater than width of said blade, and iv. a plurality of projections extending downward from said bottom surface of said body part, and b. a phallic shaped part extending generally downward from one end of said handle, and having a central longitudinal axis generally transverse of said central longitudinal axis of said handle's body part.

BRIEF DESCRIPTION OF DRAWINGS

In order to facilitate a better understanding of the nature of the present invention, a preferred embodiment of a sexual stimulation apparatus will now be described, by way of example only, with reference to the accompanying drawings in which.

BEST MODE FOR CARRYING OUT THE INVENTION

Figure 1:
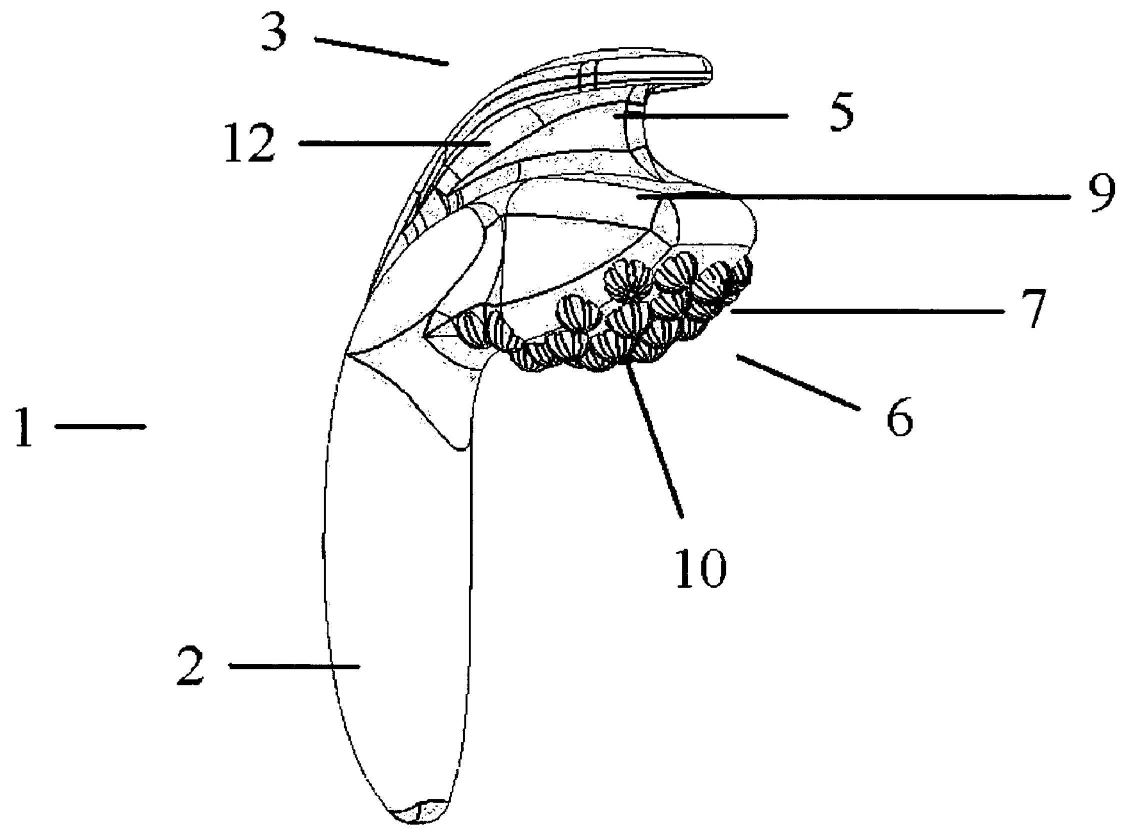
FIG. 1 depicts a side perspective view the sexual stimulation apparatus in accordance with a first embodiment of the present invention.

As shown in FIGS. 1 to 4, the sexual stimulation apparatus 1 of the present invention generally includes a phallic shaped member 2 having a handle 3 disposed at the base thereof. The handle 3 generally includes a projection member 5 and a clitoral stimulator 6.

Figure 2:
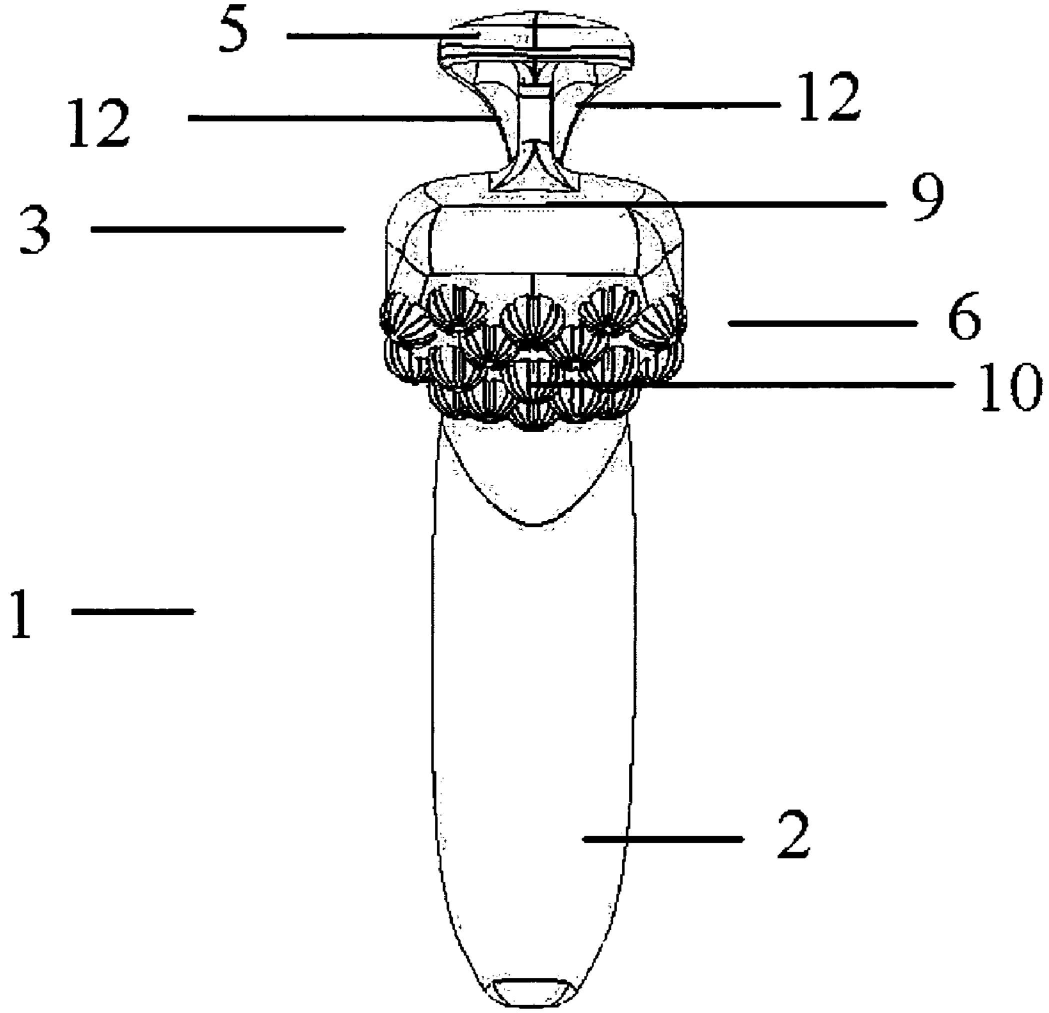
FIG. 2 depicts a rear perspective view of the embodiment of the present invention shown in FIG. 1.
Figure 3:
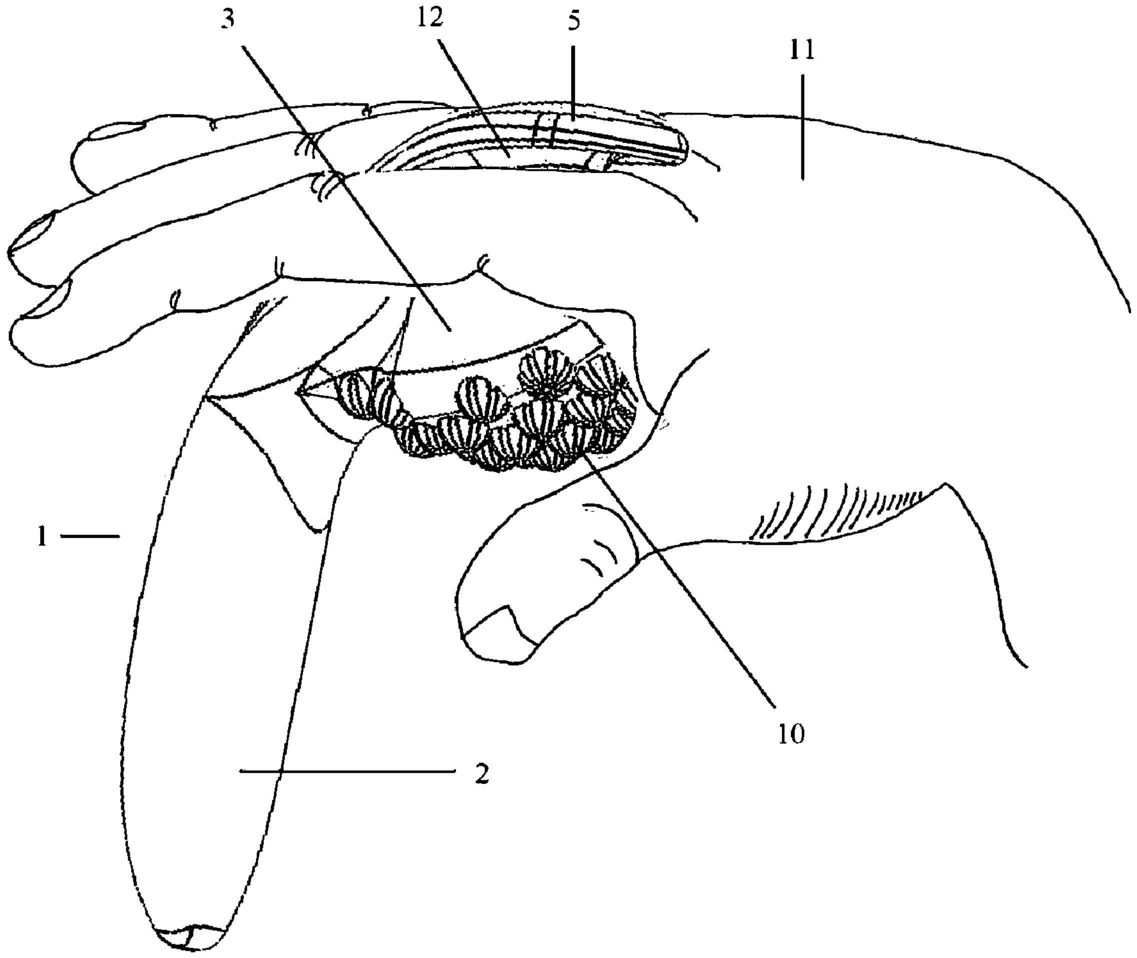
FIG. 3 depicts a side perspective view of the embodiment of the present invention shown in FIG. 1 held in a user's hand.

As best shown in FIGS. 1 to 3, the handle 3 and the phallic shaped member 2 are integrally formed from silicone. The handle 3 includes a convex surface 9 and a clitoral stimulator 6 is located on the opposing surface. The clitoral stimulator 6 comprises a plurality of spaced apart nodules 10. In use, the spaced apart nodules 10 contact the clitoris of the user 11 thereby increasing the stimulation and pleasure derived from using the sexual stimulation apparatus 1 of the present invention when masturbating. The handle 3 also acts as a definitive end portion of the sexual stimulation apparatus 1 and thereby allows an individual user 11 to fully insert the sexual stimulation apparatus into their vagina until the clitoral stimulator 6 abuts the user's clitoris and vaginal opening.

As best shown in FIGS. 1 and 2, the clitoral stimulator 6 has a cluster of nodules 7 located distally from where the phallic shaped member 2 joins with the handle 3. This cluster of nodules 7 serves to more fully stimulate the user 11 by contacting the clitoris during masturbation. The nodules 10 can be of different sizes and shapes to provide more contact with the clitoris of the user 11. Particularly, each of the nodules 10 in the cluster of nodules 7, are of different sizes.

As best shown in FIG. 3, the convex surface 9 is adapted to sit snugly against the palm of the hand of the user 11. This allows the user 11 to have greater control of the speed and direction of the sexual stimulation apparatus 1 when masturbating. The convex surface 9 also allows the user 11 to orientate their arm, and particularly their wrist, in a more natural and comfortable position when accessing their vagina with the sexual stimulation apparatus 1 when masturbating. This helps to reduce fatigue, discomfort and potential pain that may occur in the wrist, elbow, shoulder and/or back of the user 11 during masturbation. Also, because of the shape of the sexual stimulation apparatus 1 and the orientation of the sexual stimulation apparatus 1 within the hand of a user during use, the user is able to lie substantially flat on their back when masturbating. On the other hand, conventional dildos require the user to bend or crouch forward to insert conventional dildos and the like into their vagina when masturbating. As a user of the sexual stimulation apparatus 1 of the present invention is able to lie substantially flat on their back, the possibility of pain and discomfort in their back is reduced.

The shape of the sexual stimulation apparatus 1 allows an individual user to use the "palms down" technique when masturbating. Within this specification the "palms down" technique is defined as the individual user masturbating with their palm, upon which the sexual stimulation apparatus 1 is supported, facing towards their vagina. The "palms down" technique reduces fatigue, discomfort and potential pain that may occur in the wrist, elbow, shoulder and/or back of an individual user 11.

Figure 4:
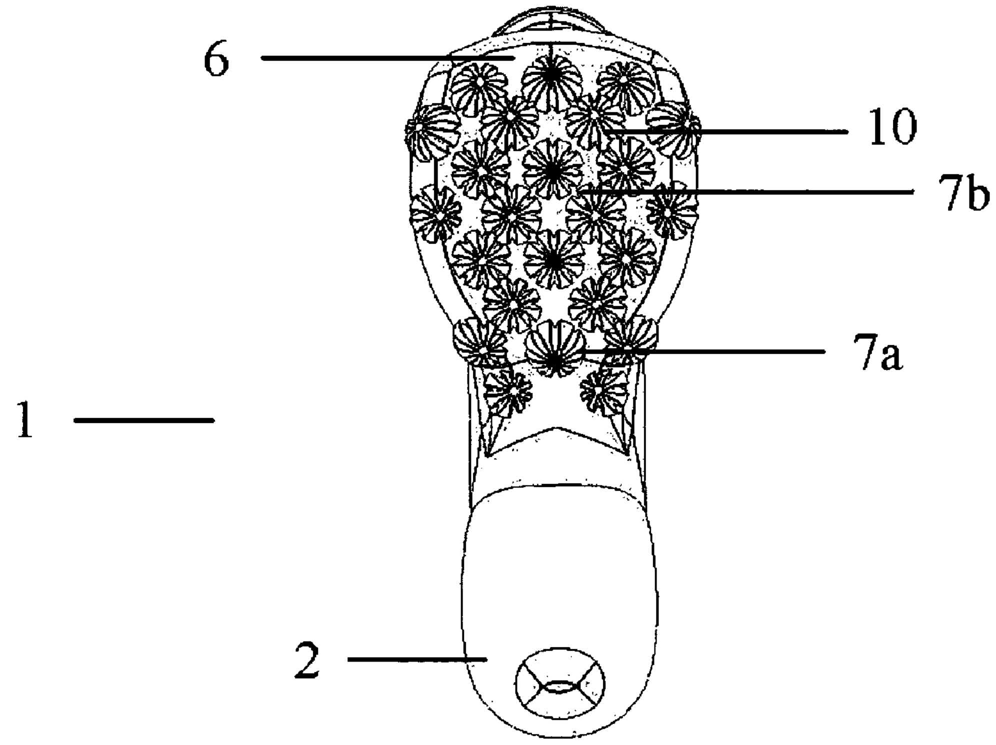
FIG. 4 depicts a bottom perspective view of a sexual stimulation in accordance with a second embodiment of the present invention.

To facilitate gripping of the handle 3, by the user 11, the convex surface 9 of the handle 3 includes a projection 5 that extends away from the convex surface 9 of the handle 3. As best shown in FIG. 4, the projection 5 is adapted to interdigitally engage with the hands of the user 11. Interdigital engagement is defined in this specification to mean that the projection 5 extends between at least two adjacent fingers of the user 11. The projection 5 is then able to be held by way of frictional engagement by the at least two adjacent fingers. To facilitate the gripping of the handle 3 in an ergonomically correct and comfortable orientation, the projection 5 is substantially curved and follows the natural contours of the user's hand. The curvature of the projection 5 allows the convex surface 9 to sit snugly against the palm and fingers of the user's hand when the sexual stimulation apparatus 1 is used in masturbation.

As best shown in FIG. 2, to compliment this interdigital engagement, the projection 5 includes a grooved section 12 that follows the contours of the curved fingers of the user 11 the sexual stimulation apparatus 1 is used when masturbating. When viewed in end view cross-section, the projection 5 is "T-shaped". This facilitates engagement between the projection 5 and the fingers of the user 11, particularly because the upper part of the "T-section" engages with the top of the fingers of the user 11. This reduces the possibility of the projection 5 from slipping out from between the fingers of the user 11 during use.

A second embodiment of the sexual stimulation apparatus 1 is shown in FIG. 4. As many of the features in this embodiment are the same as the features of the first embodiment, the same reference numerals will be used to show like features. In this second embodiment, the clitoral stimulator 6 includes two clusters of nodules 7*a* and 7*b*. This may be preferred by some users as it may provide a greater level of clitoral stimulation when using the sexual stimulation apparatus 1 during masturbation. Of course it should be understood that there may be any number of nodule clusters included on the clitoral stimulator 6. The clitoral stimulator 6 may also not have any nodule clusters.

Whilst the embodiments shown in the drawings depict the clitoral stimulator 6 comprising nodules 10, in other embodiments not shown in the drawings, the clitoral stimulator may include other forms of stimulation, rather than nodules, such as ridges or the like.

The embodiments depicted in FIGS. 1 to 4 show the phallic shaped member 2 and the handle 3 are integrally formed from silicone. However, it should be understood that any suitable material could be used to manufacture the phallic shaped member 2 and the handle 3, such as metal, plastic, glass, rubber or other suitable materials.

In other embodiments not shown in the drawings, the phallic shaped member 2 and the handle 3 may be two separate pieces. In this case, the phallic shaped member 2 and the handle 3 may be either manufactured from the same material or from different materials. For example, the handle 3 may be manufactured from a relatively rigid plastic or the like, whilst the phallic shaped member 2 may be manufactured from a more flexible material such as silicone.

In another embodiment not shown in the drawings, the sexual stimulation apparatus 1 may be a vibrator. Thus, it would be necessary to include a vibrating mechanism and a power source such as batteries in the sexual stimulation apparatus 1. In this embodiment, the phallic shaped member 2 and the handle 3 would preferably be two separate pieces that are engageable with each other. The batteries would be inserted into a hollow cavity in the phallic shaped member 2 and then the phallic shaped member 2 would be electrically engaged with the handle 3. The handle 3 would contain a vibrating mechanism that causes the sexual stimulation apparatus 1 to vibrate, thereby increasing the sexual stimulation to the user 11 when masturbating.

In embodiments where the phallic shaped member 2 and the handle 3 are two separate pieces, it should be understood that the handle 3 may engage with a range of different phallic shaped members 2, provided that they all have a common base portion that is adapted to engage with the handle 3. The user 11 may purchase a "set" including a handle 3 and a range of different phallic shaped members 2 that are adapted to engage with the handle 3. The range of different phallic shaped members may be of different shapes, lengths, materials, colours and they may or may not vibrate. The "set" may also include a number of different handles 3, each one having a differently configured clitoral stimulator 6 and/or projection 5.

Whilst the embodiments of the sexual stimulation apparatus shown in the drawings include only a single projection 5, it is within the scope of this invention that the sexual stimulation apparatus 1 may include multiple projections. Each one of the multiple projections would engage interdigitally between adjacent fingers of the hand of the user 11.

It should also be understood that whilst the projection 5 of the embodiments shown in the drawings is "T-shaped" when viewed in an end view cross-section, in other embodiments not shown in the drawings, the projection 5 may be one or more ring-like members that encircle one or more of the fingers of the hands of the user 11. The projection may also simply be protrusion that extends away from the convex surface 9 or it may be a straight protrusion having a bulbous end to facilitate gripping by the user 11. The protrusion 5 may also have a gradientally increasing thickness, whereby the distal end to the convex surface 9 has a greater thickness than the proximal end to the convex surface 9.

In another embodiment not shown in the drawings, the sexual stimulation apparatus 1 may include an anal protruding member or a testicle-shaped projection.

The invention has been described by way of non-limiting examples only and many modifications and variations may be made thereto without departing from the spirit and scope of the invention described. The essence of the invention is the handle that is disposed at the base of the phallic shaped member.

In this specification, unless the context clearly indicates otherwise, the word "comprising" is not intended to have the exclusive meaning of the word (such as "consisting only of"), but rather has the non-exclusive meaning, in the sense of "including at least". The same applies, with corresponding grammatical changes, to other forms of the word such as "comprise", etc.

It will be apparent that obvious variations or modifications may be made in accordance with the spirit of the invention that are intended to be part of the invention, and any such obvious variations or modification are therefore within the scope of the invention.

The invention claimed is:

1. A sexual stimulation apparatus comprising in its upright orientation:

a. a handle having i. a body part with top and bottom surfaces and opposite ends and length along a central longitudinal axis, and width transverse said length, ii. a blade extending longitudinally and upward from said top surface of said body part, and having width less than width of said body part, iii. a roof part atop said blade and extending lengthwise and having width greater than width of said blade, and iv. a plurality of projections extending downward from said bottom surface of said body part, and b. a phallic shaped part extending generally downward from one end of said handle, and having a central longitudinal axis generally transverse of said central longitudinal axis of said handle's body part.

2. The device according to claim 1 wherein said phallic shaped part extends in said downward direction that is generally perpendicular to said central longitudinal axis of said handle.

3. The device according to claim 1 wherein at least part of said top surface of said body part defines an upward facing convex about a generally horizontal axis that is perpendicular to said central longitudinal axis of said handle.

4. The device according to claim 3 wherein said convexly curved top surface has opposite ends and a middle part between said opposite ends, and ends of said top surface are at a lower elevation than said middle part.

5. The device according to claim 1 where said blade is centrally located on said body part.

6. The device according to claim 5 with a central vertical plane defined in said blade part, and said roof part has a central longitudinal axis in said central vertical plane of said blade.

7. The device according to claim 6 where said roof and blade, when viewed in end elevation view, define a substantially T-shape.

8. The device according to claim 1 wherein said phallic shaped part has a top end extending from said one end of said body part, and phallic shaped part extends downward from top end to an elevation below said body part bottom surface.

9. The device according to claim 1 wherein said projections comprise nodules transversely spaced apart across substantially the full width and length of said bottom surface.

10. The device according to claim 1 wherein each of said projections has a generally hemispherical shape with the curved part thereof extending generally downward.

11. The device according to claim 1 operable with a vibrating mechanism for vibrating said device, and wherein said body part defines a hollow chamber between said top and bottom surfaces to receive and hold said vibrating mechanism.

12. The device according to claim 11 where said vibrating mechanism is adapted to vibrate said device in an axial direction generally perpendicular to said central longitudinal axis of said handle.

13. The device according to claim 1 wherein said body part defines a hollow chamber between said top and bottom surfaces, said device further comprising a vibrating mechanism adapted to vibrate said device in an axial direction generally perpendicular to said central longitudinal axis of said handle.

14. The device according to claim 1 wherein said handle and said phallic shaped element are integrally formed from a single piece of material.

15. The device according to claim 14 wherein said single piece of material is injection molded silicone.

16. The device according to claim 1 wherein said handle and said phallic shaped element are formed from two separate pieces of material that are engageable with each other.

17. The device according to claim 16 wherein said handle and said phallic shaped element are formed of the same material.

18. The device according to claim 16 wherein said handle is formed of a rigid material and said phallic shaped element is formed from injection molded silicone.

* * * * *